(12) United States Patent
Ohashi et al.

(10) Patent No.: US 12,042,573 B2
(45) Date of Patent: *Jul. 23, 2024

(54) INACTIVATION DEVICE

(71) Applicant: Ushio Denki Kabushiki Kaisha, Tokyo (JP)

(72) Inventors: Hiroyuki Ohashi, Tokyo (JP); Shinji Suzuki, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/011,709

(22) PCT Filed: Aug. 2, 2021

(86) PCT No.: PCT/JP2021/028543
§ 371 (c)(1),
(2) Date: Dec. 20, 2022

(87) PCT Pub. No.: WO2022/070590
PCT Pub. Date: Apr. 7, 2022

(65) Prior Publication Data
US 2023/0302171 A1    Sep. 28, 2023

(30) Foreign Application Priority Data

Sep. 29, 2020   (JP) .................. 2020-162940

(51) Int. Cl.
*A61L 2/10*   (2006.01)
*A61L 2/24*   (2006.01)
*A61L 2/26*   (2006.01)

(52) U.S. Cl.
CPC .... *A61L 2/10* (2013.01); *A61L 2/24* (2013.01); *A61L 2/26* (2013.01); *A61L 2202/11* (2013.01);
(Continued)

(58) Field of Classification Search
CPC ..... A61L 2/10; A61L 2/24; A61L 2/26; A61L 9/28
See application file for complete search history.

(56) References Cited

U.S. PATENT DOCUMENTS 5,834,784 A * 11/1998 Morgan ............... H01J 65/046
250/435
2015/0014723 A1    1/2015 Atanackovic
(Continued)

FOREIGN PATENT DOCUMENTS

CN    105209570 A    12/2015
CN    109966652 A    7/2019
(Continued)

OTHER PUBLICATIONS

A Sterilizing Unmanned Aerial Vehicle; Cheng, Ken, Jul. 3, 2018; CN 207571586 U (Year: 2018).*
(Continued)

*Primary Examiner* — Walter D. Griffin
*Assistant Examiner* — Cameron J Allen
(74) *Attorney, Agent, or Firm* — Kenichiro Yoshida (57) ABSTRACT

An inactivation device inactivates microorganisms and/or viruses present in a space where a person is present by irradiating the space with ultraviolet light. The inactivation device includes a mobile body movable in the space, a drive section that drives the mobile body, an ultraviolet light irradiation unit provided with an ultraviolet light source emitting light including ultraviolet light having a wavelength that inactivates microorganisms and/or viruses, and a controller that controls the irradiation of the light from the ultraviolet light source. The ultraviolet light source is either an excimer lamp or an LED, and the ultraviolet light included in the light emitted from the ultraviolet light source includes ultraviolet light having a wavelength range from
(Continued)

200 nm to 240 nm. The ultraviolet light irradiation unit is fixed to the mobile body.

11 Claims, 5 Drawing Sheets

(52) U.S. Cl.
CPC ....... *A61L 2202/14* (2013.01); *A61L 2202/16* (2013.01); *A61L 2202/25* (2013.01)

(56) References Cited

U.S. PATENT DOCUMENTS

| | | |
|---|---|---|
| 2016/0317690 A1 | 11/2016 | Dayton |
| 2018/0064833 A1 | 3/2018 | Childress et al. |
| 2018/0079528 A1 | 3/2018 | Siegmeth et al. |
| 2019/0216958 A1 | 7/2019 | Kreltenberg et al. |
| 2020/0234941 A1 | 7/2020 | Yagyu et al. |
| 2021/0299311 A1 * | 9/2021 | Yu ............................ A61L 2/24 |

FOREIGN PATENT DOCUMENTS

| | | | | |
|---|---|---|---|---|
| CN | 111214680 A | | 6/2020 | |
| CN | 111588874 A | | 8/2020 | |
| CN | 112121205 A | * | 12/2020 | ............ A61L 2/10 |
| EP | 3613702 A1 | | 2/2020 | |
| JP | 2007-059667 A | | 3/2007 | |
| JP | 2017-528258 A | | 9/2017 | |
| JP | 2018-010795 A | | 1/2018 | |
| JP | 2018-069028 A | | 5/2018 | |
| JP | 2018-113116 A | | 7/2018 | |
| JP | 2018-130535 A | | 8/2018 | |
| WO | WO-2005031881 A2 | * | 4/2005 | ............ C02F 1/325 |
| WO | WO-2016049674 A1 | * | 4/2016 | ............ B01D 61/14 |
| WO | WO-2016077403 A1 | * | 5/2016 | ............ A61L 2/10 |
| WO | 2018/131582 A1 | | 7/2018 | |

OTHER PUBLICATIONS

Wayback Date (Year: 2020).*
Translation—WO 2016049674 A1 (Year: 2016).*
CN-112121205-A Translation (Year: 2020).*
Unpublished, Pending U.S. Appl. No. 18/016,309 filed Jan. 24, 2023 BY Hiroyuki Ohashi, Related to the Current Application.
PCT International Search Report for PCT/JP2021/028543, Published as WO2022070590 Including Written Opinion of the International Searching Authority, Mailed On Sep. 28, 2021.
Supplementary European Search Report For Ep 21874894.5, Mailed On Oct. 27, 2023.
222nm single-peaked deep-UV LED with thin AlGaN quantum well layers, Nogushi et al., Phys. Status Solidi C6, No. 52, S459-S461m Mar. 12, 2009.
—Nitride Based Narrow Band Far-UVC LEDs for Airborne Surface Disinfection, H.Q.T. Bui et al, ECS Transaction, 98 (6) 83-89 (2020).
Chineese Office Action For 2021800604029 With English Translation, Mailed On Jul. 15, 2023.
Unpublished, Pending U.S. Appl. No. 18/016,309 filed Jan. 13, 2021 By Hiroyuki Ohashi.
Second Chinese Office Action (OA) Mailed On Dec. 9, 2023 For CN 202180060402.9, English Translation Attached.
Taiwanese Office Action Mailed On Dec. 4, 2023 For 110132386, English Translation Attached.
Taiwanese Office Action Mailed On Dec. 5, 2023 For 110132387, English Translation Attached.

* cited by examiner

Cross section taken along the line A-A

Cross section taken along the line B-B

Cross section taken along the line C-C

INACTIVATION DEVICE

TECHNICAL FIELD

The present invention relates to an inactivation device that inactivates harmful microorganisms and/or viruses.

BACKGROUND ART

Facilities where people frequently gather or come and go, such as medical facilities, schools, government offices, theaters, hotels, and restaurants, have environments where microorganisms such as bacteria and mold can easily multiply and viruses can easily spread. In particular, this tends to be more noticeable in closed spaces (e.g., hospital rooms, restrooms, and elevators) and crowded spaces in the above facilities. For example, harmful and highly infectious microorganisms and viruses can multiply on the floor, walls, and other surfaces of a given space, or float within the space, as a person infected with such microorganisms and/or viruses enter and leave the space. This can result in the spread of the microorganisms and/or viruses to the next person who enters the space, and in some cases, the spread of infectious diseases within the facility.

To address the above situations, facilities where people (and in some cases animals) gather or come and go are required to take measures to disinfect the above-mentioned harmful microorganisms (e.g., infectious microorganisms) or inactivate viruses. Surfaces surrounding the above spaces, such as floors and walls, are decontaminated by workers, for example, by spraying them with disinfectants including alcohol, wiping them with disinfectant-soaked cloths, or irradiating them with germicidal ultraviolet light. Microorganisms and viruses floating in the spaces are disinfected and inactivated by ultraviolet light irradiation, for example.

Patent document 1 (JP-T-2017-528258) discloses a decontamination device for decontaminating a closed room in which a space to be decontaminated is irradiated with ultraviolet light (UVC light) emitted from a UVC bulb to disinfect the space. In addition, Patent Document 2 (JP-A-2018-069028) discloses a device for disinfecting surfaces in an enclosed space by emitting ultraviolet light from arc lights, lasers, light-emitting diodes (LED), micro-filaments, optical fiber elements, light bulbs, or other UV light-emitting devices.

CITATION LIST

Patent Document 1: JP-T-2017-528258
Patent Document 2: JP-A-2018-069028

SUMMARY OF INVENTION

Technical Problem

The wavelength band of ultraviolet light used for decontamination (disinfection) applications practically ranges from 200 nm to 320 nm. In particular, the effective wavelength for disinfection is around 260 nm, which is absorbed by nucleic acids (DNA, RNA) possessed by microorganisms and viruses. Hence, low-pressure mercury lamps that emit ultraviolet light having a wavelength of 253.7 nm are often used as light sources for disinfection.

However, low-pressure mercury lamps have characteristics that the illuminance of its emitted ultraviolet light becomes unstable when they are subjected to vibration. For example, when an ultraviolet light source for inactivating microorganisms or viruses is mounted on a mobile body, the ultraviolet light source is subjected to vibration while the vehicle is moving. If the ultraviolet light source is a low-pressure mercury lamp, this vibration causes the illuminance of the ultraviolet light emitted from the low-pressure mercury lamp to become unstable, thus in some cases, potentially leading to the insufficient disinfection and inactivation treatment of the object to be inactivated.

In recent years, LEDs emitting ultraviolet light having a peak wavelength of, for example, 275 nm have also been employed as an ultraviolet light source for disinfection and inactivation. However, ultraviolet light having a wavelength of 275 nm emitted from the above-mentioned ultraviolet LED and the ultraviolet light having a wavelength of around 260 nm, such as the ultraviolet light having a wavelength of 253.7 nm emitted from the above-mentioned low-pressure mercury lamp, may have adverse effects on human bodies although they are highly effective in disinfection and inactivation. Hence, this ultraviolet light is not suitable for performing decontamination work in a space where a person is present, like the techniques described in the above-mentioned documents.

In view of these circumstances, the present invention is to provide an inactivation device that is capable of stably emitting ultraviolet light in a space where a person is present and properly inactivating harmful microorganisms and/or viruses.

Solution to Problem

In order to solve the above problem, an aspect of the inactivation device according to the present invention is an inactivation device that inactivates microorganisms and/or viruses present in a space where a person is present by irradiating the space with ultraviolet light, the inactivation device includes:
 a mobile body movable in the space;
 a drive section that drives the mobile body;
 an ultraviolet light irradiation unit provided with an ultraviolet light source emitting light including ultraviolet light having a wavelength that inactivates the microorganisms and/or viruses; and
 a controller that controls the irradiation of the light from the ultraviolet light source. The ultraviolet light source is either an excimer lamp or an LED, and the ultraviolet light included in the light emitted from the ultraviolet light source includes ultraviolet light having a wavelength range from 200 nm to 240 nm. The ultraviolet light irradiation unit is fixed to the mobile body. This configuration enables the ultraviolet light to radiate in a space where a mobile body, such as a drone or a cleaning robot, is movable, performing inactivation treatment. This configuration, even when the ultraviolet light irradiation unit (ultraviolet light source) is subject to vibration while the mobile body is moving, enables the ultraviolet light source to stably emit the ultraviolet light.

In addition, in the above inactivation device described, the drive section may be configured to move the mobile body in any two-dimensional direction. This configuration enables the ultraviolet light irradiation unit to be mounted on, for example, a cleaning robot that moves on the floor surface to perform decontamination work. In the above inactivation device, the drive section may be configured to move the mobile body in any three-dimensional direction. This configuration enables the ultraviolet light irradiation unit to be mounted on, for example, a drone that moves in a predetermined three-dimensional space to perform decontamination work.

In addition, in the above inactivation device, the ultraviolet light source may be an excimer lamp including a discharge container filled with gas for excimer luminescence and a pair of electrodes that make a dielectric barrier discharge generated inside the discharge container, and at least one of the electrodes may be printed or deposited on the outer surface of the discharge container. This configuration, even when the excimer lamp is subject to vibration, prevents a gap between the electrode (external electrode) disposed on the outer front surface of the discharge container and the discharge container, suppressing fluctuation in the illuminance of ultraviolet light emitted from the excimer lamp.

In addition, in the above inactivation device, the ultraviolet light source may be an excimer lamp including a discharge container filled with gas for excimer luminescence and a pair of electrodes that make a dielectric barrier discharge generated inside the discharge container, and at least one of the electrodes is disposed to be in contact with the discharge container. The ultraviolet light irradiation unit may be provided with a vibration isolation mechanism that suppresses the vibration of the excimer lamp. This configuration, even when the excimer lamp is subject to vibration, enables the excimer lamp to be almost unaffected by the vibration, suppressing the occurrence of a gap between the discharge container and the external electrode. Therefore, ultraviolet light can be stably emitted.

In addition, in the above inactivation device, the ultraviolet light source may be an excimer lamp, and the ultraviolet light irradiation unit may include an enclosure that houses the excimer lamp and is made of a conductive metal. This configuration prevents high-frequency noise generated from the excimer lamp from being transmitted outside the enclosure. This, in turn, can suppress control commands to the control system provided outside the enclosure from being interfered by the high-frequency noise emitted from the excimer lamp, thereby suppressing malfunctions in the control commands.

In addition, in the above inactivation device, the ultraviolet light source may be an LED, and the LED may be either an aluminum-gallium-nitride (AlGaN)-based LED or an aluminum-nitride (AlN)-based LED. It may also be a magnesium-zinc-oxide (MgZnO)-based LED. This configuration can use LEDs that are less susceptible to vibration, changes in atmospheric pressure, and changes in temperature, emitting ultraviolet light in the wavelength range from 200 nm to 240 nm, which has less adverse effects on human bodies, and properly inactivating microorganisms and/or viruses. Moreover, unlike the case in which the ultraviolet light source is an excimer lamp, this configuration eliminates the need for the measure to suppress the occurrence of a gap between the discharge container and the external electrode.

In addition, in the above inactivation device, the ultraviolet light source may be an LED, and the ultraviolet light irradiation unit may include a cooling member that cools the LED. This configuration suitably suppresses the increase in the temperature of the LED, thus the LED can stably emit light.

In addition, in the above inactivation device, the ultraviolet light irradiation unit may include an enclosure that houses the ultraviolet light source thereinside and that includes a light emission window through which at least a part of the light emitted from the ultraviolet light source is emitted, and the light emission window may be provided with an optical filter that blocks the transmission of UV-C waves having longer wavelengths than 237 nm. This configuration enables the ultraviolet light irradiation unit to radiate only light having a wavelength band with less adverse effects on human bodies and animals.

In addition, in the above inactivation device, the ultraviolet light source may emit ultraviolet light having a center wavelength of 222 nm. This configuration effectively inactivates microorganisms and/or viruses while suitably suppressing the adverse effects of ultraviolet light irradiation on human bodies.

Effects of the Invention

The present invention is capable of suitably inactivating harmful microorganisms and/or viruses by irradiating a space where a person is present with ultraviolet light. The objects, modes, and effects of the present invention described above and those not described above will be understood by those skilled in the art from the following description of embodiments (detailed description of the invention) with reference to the accompanying drawings and claims.

DESCRIPTION OF EMBODIMENTS

Hereinafter, the embodiment of the present invention will be described with reference to the drawings. The present embodiment describes an inactivation device that performs ultraviolet light irradiation in a space where a person is present to inactivate microorganisms and/or viruses present in the space. The "space where a person is present" is not limited to a space where a person is actually present; it includes a space where a person enters and leaves, but where no one is present. In addition, "inactivation" according to the present embodiment refers to eliminating microorganisms and/or viruses (or making them lose their infectivity or toxicity).

Here, examples of the above spaces include spaces in facilities such as offices, commercial facilities, medical facilities, station facilities, schools, government offices, theaters, hotels, and restaurants, as well as spaces for mobility means such as automobiles, trains, buses, cabs, airplanes, and ships. The above spaces may be closed spaces a person can enter and leave, such as hospital rooms, meeting rooms, guest rooms, restrooms, and rooms in elevators, or unclosed spaces. The above mobility means can be any means of transporting people or objects, and is not limited to transportation means.

The inactivation device in the present embodiment inactivates harmful microorganisms and/or viruses present on the surface of objects and in a space where a person is present by irradiating them with ultraviolet light having a wavelength from 200 to 240 nm that is less adverse effects on cells of human bodies and animals. Here, the above objects include human bodies, animals, and things. The inactivation device in the present embodiment is used under an environment subject to vibration.

Figure 1:
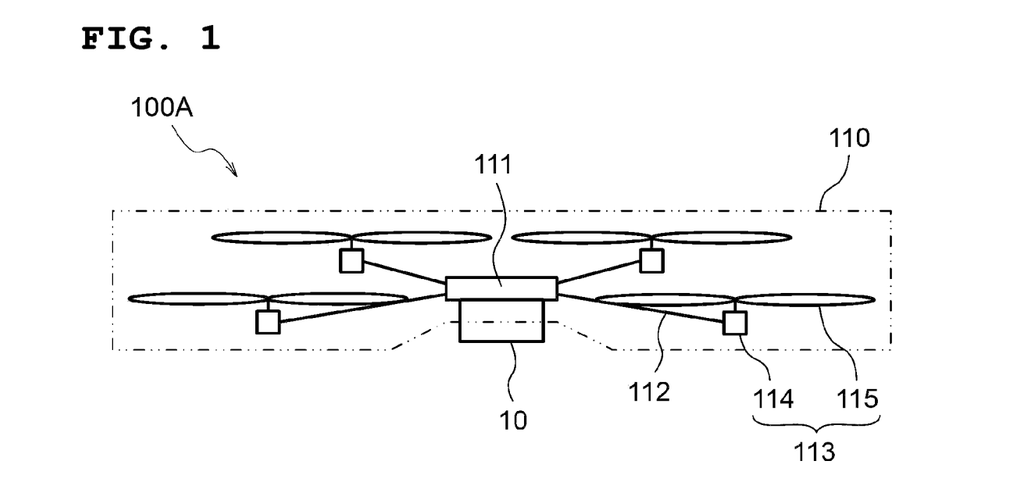
FIG. 1 is a schematic diagram illustrating a configuration example of an inactivation device in which an ultraviolet light irradiation unit is mounted on a flying object.

FIG. 1 is a schematic diagram illustrating a configuration example of an inactivation device 100A in which an ultraviolet light irradiation unit 10 is mounted on a flying object 110. The flying object 110 is a mobile body that is movable in any three-dimensional direction in a space where a person is present, for example, a drone (multicopter). This inactivation device 100A includes an ultraviolet light irradiation unit 10 and the flying object 110. The ultraviolet light irradiation unit 10 is provided with an ultraviolet light source that emits light including ultraviolet light in the wavelength range from 200 nm to 240 nm, which is ultraviolet light for disinfection and inactivation. The ultraviolet light irradiation unit 10 is supported by a supporter (in this case, a body section 111) provided in the flying object 110.

The flying object 110 includes the body section 111 and a plurality (four in the present embodiment) of frame sections 112 extending from the body section 111. In addition, the flying object 110 includes driving sections 113 each provided at the end of the respective frame sections 112 (the end that is not located at the side of the body section 111). The drive section 113 is a propulsion drive section that generates lift and thrust for the flight of the flying object 110 and includes a motor 114 and rotor blades (also called propellers or rotors) 115 that are rotated by the motor 114. Here, the motor 114 can use a variable speed motor or a single speed motor. Each motor 114 can be driven independently.

The present embodiment uses a propeller drive with the motor 114 as a drive section that drives the flying object 110; however, the drive section is not limited to this, and it can also use a drive mechanism such as a gas jet, for example.

The body section 111 is provided with a control system and a power supply, which are omitted in the figure. The control system has the function of driving the motors 114 to rotate the rotor blades 115, and controlling the lift and thrust of the flying object 110. Control commands to the control system can be given via wired or wireless communication from an external control system that controls the operation of the flying object 110. For example, the operator operates the controller (external control system) at hand to move the flying object 110 in any three-dimensional direction in a given space via wireless communication.

The flying object 110 may include a camera, a sensor, or other devices. The camera takes pictures in front of the flying object 110 in its traveling direction, for example, and can use digital cameras, video cameras, or the like. The camera may be used to capture images, video recordings, and other data. The sensor detects obstacles around the flying object 110, for example, and can include pressure sensors, accelerometers, compasses, motion sensors, proximity sensors, or any combination thereof. This configuration also enables the control system to control the position of the flying object 110 based on the data acquired by the camera, sensor, or the like.

The ultraviolet light irradiation unit 10 is supported on the lower part of the body section 111 of the flying object 110 and radiates ultraviolet light to the space and surfaces surrounding the space while flying with the flying object 110 in the space. The above-mentioned control system controls the irradiation and non-irradiation of ultraviolet light from the ultraviolet light irradiation unit 10 and the light intensity of the ultraviolet light emitted from the ultraviolet light irradiation unit 10. The ultraviolet light irradiation unit 10 may be configured to be directly controlled by the external control system described above.

In this way, the inactivation device 100A emits ultraviolet light having a wavelength range from 200 nm to 240 nm while moving in any three-dimensional direction in a space where people are present. Therefore, the inactivation device 100A suitably inactivates harmful microorganisms and/or viruses in the space and on the surfaces surrounding the space that are irradiated with ultraviolet light.

Figure 2A:
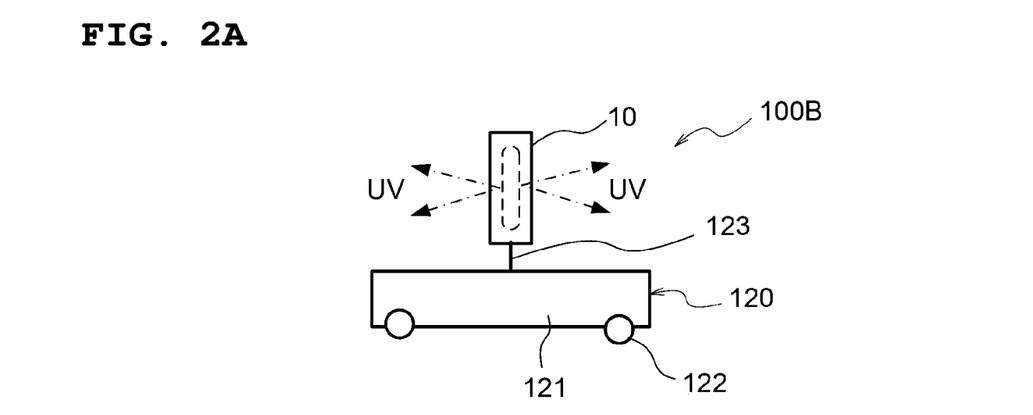
FIG. 2A is a schematic diagram illustrating a configuration example of an inactivation device in which an ultraviolet light irradiation unit is mounted on a mobile body.

FIG. 2A is a schematic diagram illustrating a configuration example of an inactivation device 100B in which the ultraviolet light irradiation unit 10 is mounted on a mobile body 120. The mobile body 120 is movable in any two-dimensional direction in a space where a person is present and is a cleaning robot that is movable on a floor surface, for example. The inactivation device 100B includes the ultraviolet light irradiation unit 10 and the mobile body 120. The ultraviolet light irradiation unit 10 has the configurations same as those of the ultraviolet light irradiation unit 10 provided in the inactivation device 100A in FIG. 1 described above. The ultraviolet light irradiation unit 10 is supported by a supporter (in this case, a supporter 123) provided in the mobile body 120.

The mobile body 120 includes a body section 121 and wheels 122 rotatably supported in the body section 121. The body section 121 is provided with, as a drive section that drives the mobile body 120 although not specifically shown in the figure, a motor that rotates the wheels 122, and a wheel adjustment mechanism that adjusts the direction of the wheels 122. In addition, the body section 121 is provided with a control system and a power supply, which are omitted in the figure. The control system has the function of driving the above motor to rotate the wheels 122, and adjusting the above wheel adjustment mechanism to control the orientation of the wheels 122.

Control commands to the control system can be given via wired or wireless communication from an external control system that controls the movement of the mobile body 120. For example, the operator operates a controller (external control system) at hand to move the mobile body 120 in any two-dimensional direction in a given space via wireless communication.

The mobile body 120 may include a camera, a sensor, or other devices. The camera takes pictures in front of the mobile body 120 in its traveling direction, for example, and can use digital cameras, video cameras, or the like. The camera may be used to capture images, video recordings, and other data. The sensor detects obstacles around the mobile body 120, for example, and can include pressure sensors, accelerometers, compasses, motion sensors, proximity sensors, or any combination thereof. This configuration also enables the control system to control the position of the mobile body 120 based on the data acquired by the camera, sensors, or the like.

The ultraviolet light irradiation unit 10 is supported on the body section 121 of the mobile body 120 via the supporter 123 and radiates ultraviolet light to the space and surfaces surrounding the space while moving in the space together with the mobile body 120. The above-mentioned control system controls the irradiation and non-irradiation of ultraviolet light from the ultraviolet light irradiation unit 10 and the light intensity of the ultraviolet light emitted from the ultraviolet light irradiation unit 10. The ultraviolet light irradiation unit 10 may be configured to be directly controlled by the external control system described above.

Figure 2B:
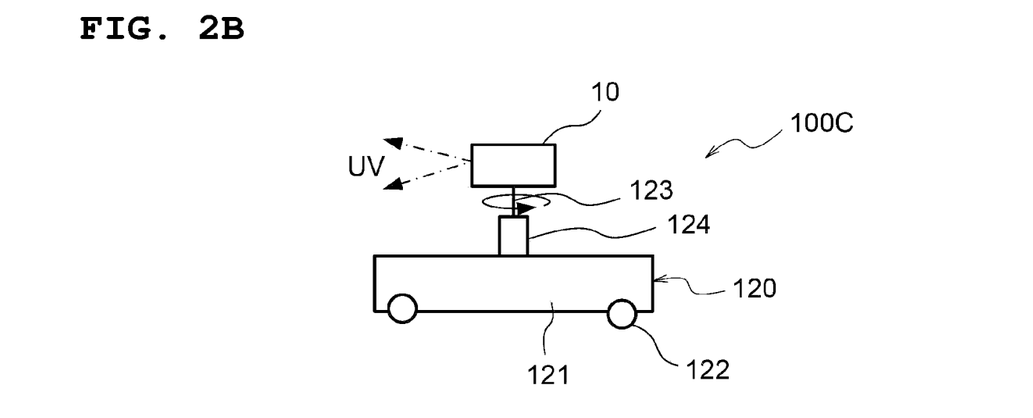
FIG. 2B is a schematic diagram illustrating a configuration example of an inactivation device in which an ultraviolet light irradiation unit is mounted on a mobile body.

Here, the ultraviolet light (UV) emitted from the ultraviolet light irradiation unit 10 may be emitted in all directions as shown in FIG. 2A or may be emitted only in a predetermined direction in the inactivation device 100C shown in FIG. 2B. The inactivation device 100C shown in FIG. 2B may include an irradiation direction adjustment mechanism 124 that adjusts the direction of the ultraviolet light irradiation unit 10, which emits ultraviolet light in a predetermined direction. The irradiation direction adjustment mechanism 124 is a motor connected to the ultraviolet light irradiation unit 10, for example, and rotates the ultraviolet light irradiation unit 10 by a predetermined angle, thus adjusting the direction of the ultraviolet light emitted from the ultraviolet light irradiation unit 10.

In this way, the inactivation devices 100B and 100C emit ultraviolet light in the wavelength range from 200 nm to 240 nm while moving in any two-dimensional direction in a space where a person is present. Therefore, the inactivation devices are capable of suitably inactivating harmful microorganisms and/or viruses present in a space and on surfaces surrounding the space that are irradiated with ultraviolet light.

Figure 3:
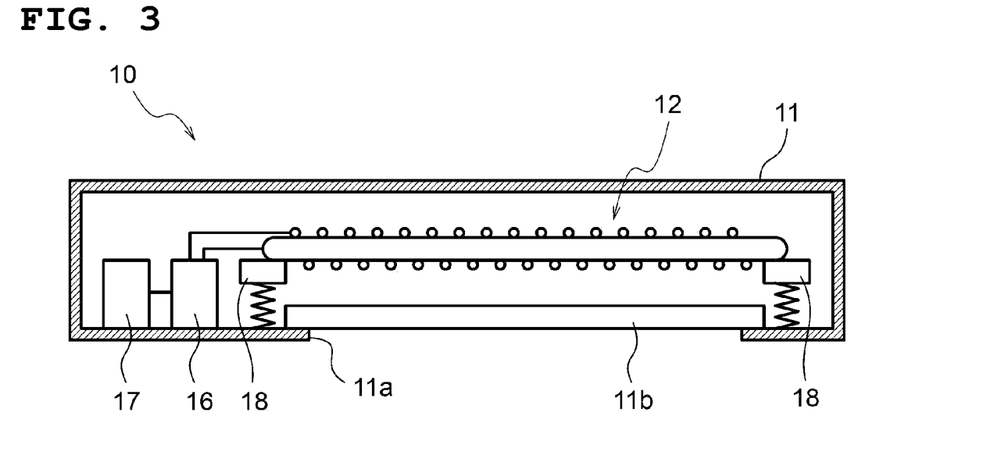
FIG. 3 is a schematic diagram illustrating a configuration example of an ultraviolet light irradiation unit.

FIG. 3 is a schematic diagram illustrating a configuration example of the ultraviolet irradiation unit 10 provided in the respective inactivation devices 100A to 100C. The present embodiment describes the case in which the ultraviolet light irradiation unit 10, which is provided in the respective inactivation devices 100A to 100C, has the same configuration. The ultraviolet light irradiation unit 10 includes an enclosure 11 made of conductive metal and an ultraviolet light source 12 housed inside the enclosure 11. The ultraviolet light source 12 can be a KrCl excimer lamp emitting ultraviolet light having a center wavelength of 222 nm, for example. The ultraviolet light source 12 is not limited to a KrCl excimer lamp and can be any light source emitting ultraviolet light in the wavelength range from 200 nm to 240 nm.

The ultraviolet light irradiation unit 10 also includes a power supply 16 that supplies power to the excimer lamp 12, and a controller 17 that controls the irradiation and non-irradiation of the excimer lamp 12, the amount of ultraviolet light emitted from the excimer lamp 12, and the like. The excimer lamp 12 is supported by a vibration isolator 18 in the enclosure 11. The excimer lamp 12 is supported by a vibration isolation member 18 in the enclosure 11. The enclosure 11 has an opening 11a that serves as a light emission window. This opening 11a is provided with a window member 11b. The window member 11b can include, for example, an ultraviolet light transmitting member made of quartz glass or an optical filter that blocks undesirable light. The plurality of excimer lamps 12 can be arranged in the enclosure 11. The number of the excimer lamps 12 can be any number.

The above optical filter can use, for example, a wavelength selective filter that transmits light in a wavelength band of 200 nm to 237 nm and blocks light in the other wavelength band among the UV-C wavelength band (200 nm to 280 nm). Examples of the wavelength selective filter include a dielectric multilayer filter consisting of $HfO_2$ layers and $SiO_2$ layers. Providing an optical filter in the light emission window, even if the excimer lamp 12 emits a small amount of light harmful to humans, is capable of reliably suppressing the light from leaking out of the enclosure 11.

In addition, the wavelength selective filter can use an optical filter having a dielectric multilayer film consisting of $SiO_2$ layers and $Al_2O_3$ layers. However, an optical filter having a dielectric multilayer film made of $HfO_2$ layers and $SiO_2$ layers can have a smaller number of the total layers than that of the dielectric multilayer film consisting of $SiO_2$ layers and $Al_2O_3$ layers. Hence, an optical filter having a dielectric multilayer film made of $HfO_2$ layers and $SiO_2$ layers can have a higher transmittance of ultraviolet light at an incident angle of 0°.

Figure 4A:
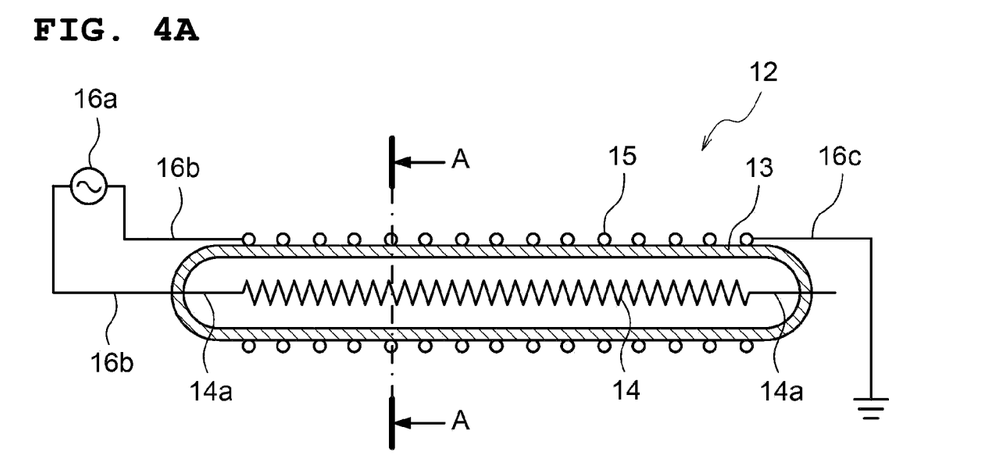
FIG. 4A is a schematic diagram illustrating a configuration example of an excimer lamp.
Figure 4B:
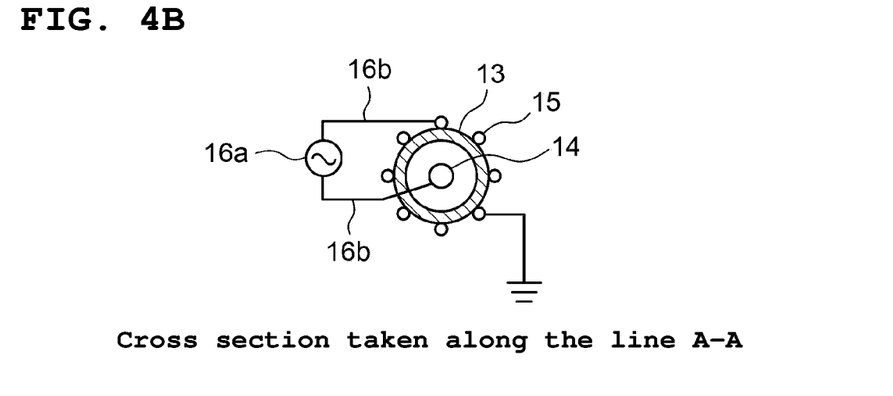
FIG. 4B is a cross-sectional view of the excimer lamp in FIG. 4A taken along the line A-A.

Hereinafter, the configuration example of the excimer lamp 12 used as an ultraviolet light source in the ultraviolet light irradiation unit 10 is specifically described. FIG. 4A is a schematic diagram of a cross section of the excimer lamp 12 in the direction of the tube axis thereof, and FIG. 4B is a cross-sectional view taken along the line A-A. As shown in FIGS. 4A and 4B, the excimer lamp 12 includes a long straight circular discharge container 13 with its both ends hermetically sealed. The discharge container 13 is made of a dielectric material with ultraviolet light transparency, such as synthetic quartz glass or fused quartz glass. A discharge space is formed inside the discharge container 13, and this discharge space is filled with a noble gas and a halogen gas as a barrier discharge gas (hereinafter referred to as the "discharge gas") that generates ultraviolet light. In the present embodiment, krypton (Kr) is used as a noble gas and chlorine gas ($Cl_2$) is used as a halogen gas. A mixture gas of krypton (Kr) and bromine ($Br_2$) can also be used as the discharge gas. In this case, the excimer lamp (KrBr excimer lamp) emits ultraviolet light having a center wavelength of 207 nm.

In addition, a first electrode (internal electrode) 14 is disposed in the discharge space inside the discharge container 13. The internal electrode 14 is a coil-shaped electrode formed by winding a metal wire made of an electrically conductive and heat-resistant metal, such as tungsten, into a coil shape with a coil diameter smaller than the internal diameter of the discharge container 13. The internal electrode 14 extends along the central axis (tube axis) of the discharge container 13 and is disposed in a manner that it fails to be in contact with the internal circumferential face of the discharge container 13. Each of the both ends of the internal electrode is connected to one end of a lead member 14a for the internal electrode. The other end of the lead member 14a for the internal electrode protrudes outwardly from the outer end face of the discharge container 13.

A second electrode (external electrode) 15 is provided on the outer periphery of the discharge container 13. The external electrode 15 is a mesh-shaped electrode composed of a metal strand made of an electrically conductive and heat-resistant metal such as tungsten, for example. The external electrode 15 is provided along the outer periphery of the discharge container 13, extending in the direction of the central axis of the discharge container 13. In the excimer lamp 12 shown in FIGS. 4A and 4B, the external electrode 15, which is a mesh-shaped electrode, has a cylindrical outer shape and is provided in close contact with the outer periphery of the discharge container 13. This configuration allows a discharge space to be formed in an area between the internal electrode 14 and the external electrode 15 via the tube wall (dielectric material wall) of the discharge container 13.

Furthermore, one end of the external electrode 15 and the other end of one lead member 14a for the internal electrode are each connected to a high-frequency power supply 16a provided in the power supply 16 (see FIG. 3) via a power supply wire 16b. The high-frequency power supply 16a is a power supply capable of applying a high-frequency voltage between the internal electrode 14 and the external electrode 15. The other end of the external electrode 15 is electrically connected to one end of a lead wire 16c. The other end of lead 16c is grounded. In other words, the external electrode 15 is grounded through the lead wire 16c. In the excimer lamp 12 shown in this FIGS. 4A and 4B, the one lead member 14a for the internal electrode is integrated with the power supply wire 16b.

Applying high-frequency power between the internal electrode 14 and the external electrode 15 generates a dielectric barrier discharge in the discharge space. This dielectric barrier discharge excites the atoms of the discharge gas (barrier discharge gas) sealed in the discharge space, generating excited dimers (exciplex). When these excited dimers return to their original state (ground state), a unique luminescence (excimer luminescence) is generated. In other words, the above discharge gas is an excimer luminescence gas.

Figure 5A:
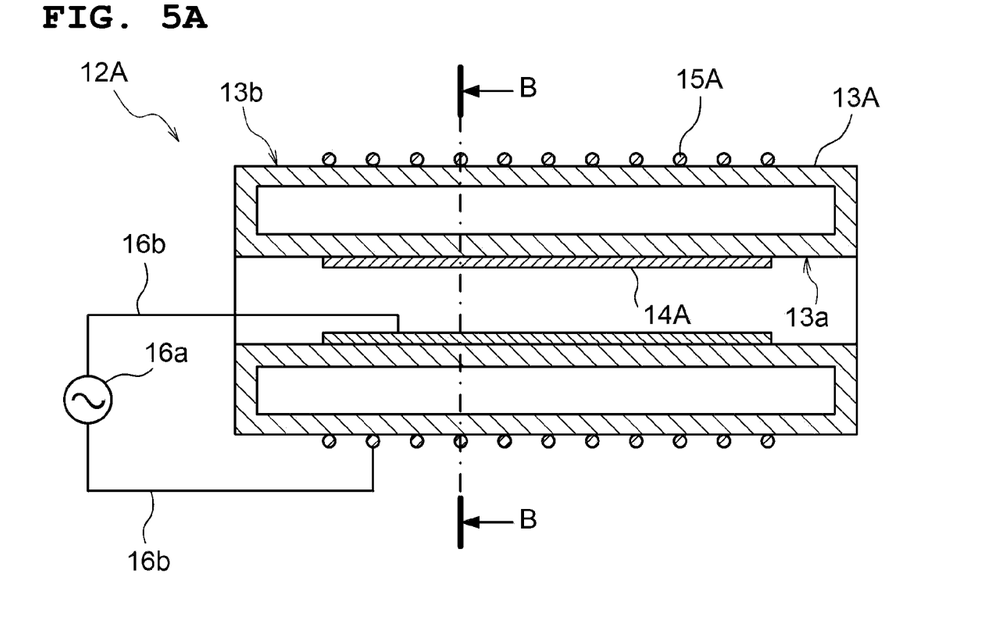
FIG. 5A is a schematic diagram illustrating another configuration example of an excimer lamp.
Figure 5B:
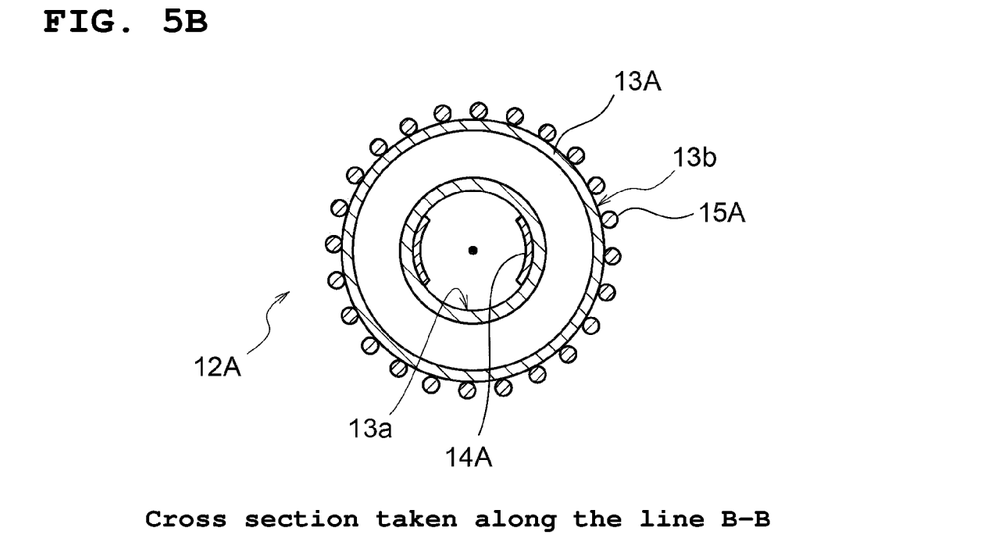
FIG. 5B is a cross-sectional view of the excimer lamp in FIG. 5A taken along the line B-B.

The configuration of the excimer lamp is not limited to those shown in FIGS. 4A and 4B; the excimer lamp can be configured to be a double-tube structure discharge container 13A as is an excimer lamp 12A shown in FIGS. 5A and 5B, for example. FIG. 5B is a cross-sectional view in FIG. 5A taken along the line B-B. The discharge container 13A of the excimer lamp 12A consists of a cylindrical outer tube and a cylindrical inner tube that has a smaller inner diameter than that of the outer tube and is coaxially disposed within the outer tube. The outer tube and the inner tube are sealed at both ends of FIG. 5A in the transverse direction, forming an annular internal space between them. The internal space is filled with discharge gas.

A layered first electrode (inner electrode) 14A is provided on an inner wall face 13a of the inner tube. A mesh or mesh-like second electrode (outer electrode) 15A is provided on an outer wall face 13b of the outer tube. The inner electrode 14A and the outer electrode 15A are each electrically connected to the high-frequency power supply 16A via the power supply wire 16b.

When the high-frequency power supply 16a applies a high-frequency alternating voltage between the inner electrode 14A and the outer electrode 15A, a voltage is applied to the discharge gas through the outer tube body and the inner tube body, generating a dielectric barrier discharge in the discharge space in which the discharge gas is sealed. This excites the atoms of the discharge gas to form excited dimers, generating excimer luminescence during the transition of these atoms to the ground state.

Figure 6A:
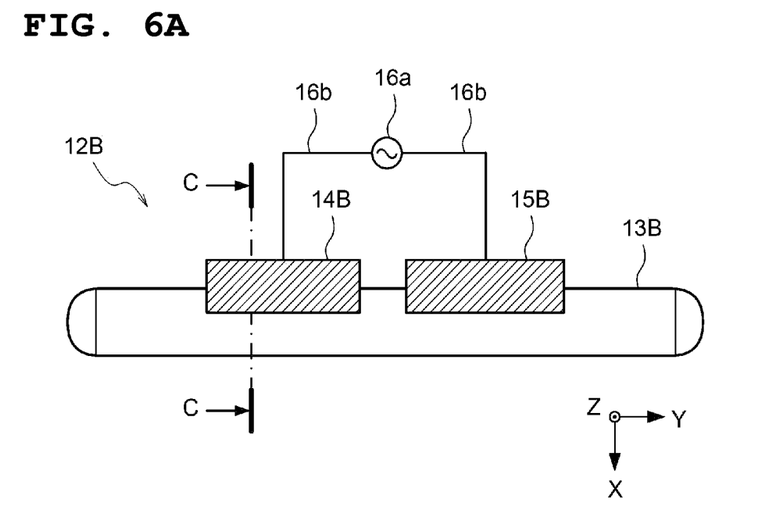
FIG. 6A is a schematic diagram illustrating yet another configuration example of an excimer lamp.
Figure 6B:
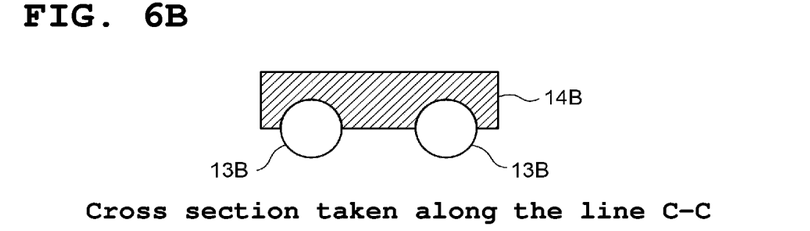
FIG. 6B is a cross-sectional view of the excimer lamp in FIG. 6A taken along the line C-C.

The configuration of the excimer lamp can be a pair of electrodes (first electrode 14B, second electrode 15B) disposed on one side face of the discharge container 13B as in the excimer lamp 12B shown in FIGS. 6A and 6B. Here, FIG. 6A shows the two discharge containers 13B arranged side by side in the Z direction, for example. FIG. 6B is a cross-sectional view in FIG. 6A taken along the line C-C. As shown in FIG. 6A, the first electrode 14B and the second electrode 15B are disposed on the side face of the discharge container 13B that is opposite a light extraction face (the face in the −X direction) and are apart from each other in the direction of the tube axis (Y direction) of the discharge container 13B. The discharge containers 13B are in contact with these two electrodes 14B and 15B in a manner of straddling them. Specifically, the two electrodes 14B and 15B each are formed with concave grooves extending in the Y direction. The discharge containers 13B are fitted into the concave grooves of the electrodes 14B and 15B.

The first electrode 14B and the second electrode 15B are each electrically connected to a high-frequency power supply 16A via the power supply wire 16b. Applying a high-frequency alternating voltage between the first electrode 14B and the second electrode 15B generates excited dimers in the internal space of the discharge container 13B, emitting excimer light from the light extraction face (the face in the +X direction) of the excimer lamp 12B. Here, the electrodes 14B and 15B may be made of a metallic material having reflectivity to the light emitted from the excimer lamp 12B. This configuration allows the light emitted from the discharge container 13B in the −X direction to be reflected and travel in the +X direction. The electrodes 14B and 15B can be made of aluminum (Al) or stainless steel, for example.

The excimer lamps generate high-frequency noise because, as described above, high-frequency power is applied to them for performing high-frequency lighting. However, configuring the enclosure 11 that houses the excimer lamp to be made of conductive metal suppresses the high-frequency noise of the excimer lamp from being transmitted outside the enclosure 11. This configuration can suppress the control commands to other control systems mounted in the vicinity of the ultraviolet light irradiation unit 10 from being disturbed by the high-frequency noise, thereby preventing malfunctions in the control commands.

In the inactivation devices 100A to 100C described above, for example, the control commands to the control system are transmitted via wireless communication by the external control system that drives the operation of the mobile bodies (flying object 110, mobile body 120). At this time, if high-frequency noise from the excimer lamp is transmitted outside the enclosure 11, disturbances caused by the high-frequency noise may cause malfunctions in the control commands to the control system. Configuring the enclosure 11 that houses the excimer lamp to be made of conductive metal prevents the above-mentioned malfunctions in the control commands to the control system, appropriately driving and controlling the operation of the mobile body.

In addition, as in the inactivation devices 100A-100C described above, when the ultraviolet light irradiation device 10 is mounted on the flying object 110 or the mobile body 120, the ultraviolet light irradiation unit 10 is subjected to vibration during the flight of the flying object 110 or the movement of the mobile body 120. Here, low-pressure mercury lamps emitting ultraviolet light with a wavelength of 253.7 nm have conventionally been used as the ultraviolet light source. The low-pressure mercury lamp has a configuration in which a noble gas such as argon (Ar) and mercury (Hg) or an amalgam thereof are enclosed in a bulb made of glass with ultraviolet light transparency. Mercury is excited by generating a discharge in the bulb. This discharge in the bulb is generated by supplying power to a pair of electrodes disposed inside the bulb or by applying high frequency to the bulb without using electrodes inside the bulb. The amount of mercury sealed inside the bulb is generally larger than that required to emit light. Hence, liquid mercury is located at the coldest point of the bulb even while the lamp is on.

When a low-pressure mercury lamp is subjected to vibration, the vibration causes the mercury in the bulb to move. The mercury moving into the discharge area evaporates, which makes the discharge unstable. In other words, when the low-pressure mercury lamp is subjected to vibration, the emitted ultraviolet light illuminance becomes unstable. This poses a possibility that the use of low-pressure mercury lamps as ultraviolet light sources in the inactivation devices mounted on the mobile bodies fails to perform disinfection and inactivation appropriately. In contrast, the inactivation devices 100A-100C in the present embodiment use excimer lamps as ultraviolet light sources. Excimer lamps are less susceptible to vibration and less prone to unstable ultraviolet light illumination even when subjected to vibration because their discharge gases are noble gases and halogen gases, which do not become liquid like mercury even at room temperature. Therefore, the use of excimer lamps is capable of performing disinfection and inactivation appropriately.

In excimer lamps, however, the electrodes (external electrodes) are provided in close contact with the outer periphery of the discharge container. When the excimer lamp is subjected to the above vibration, a gap may be created between the external electrode and the discharge container by the vibration. This gap fluctuates with the vibration. Hence, when high-frequency power is applied between a pair of electrodes to generate a dielectric barrier discharge in the discharge space, the fluctuation of this gap may cause fluctuation in the dielectric barrier discharge, possibly resulting in fluctuation in the illuminance of the ultraviolet light emitted from the excimer lamp. In addition, electric discharge occurring in the above gap may excite oxygen in the air to generate ozone, and the generated ozone may oxidize the electrical components in the ultraviolet light irradiation unit.

To address this concern, the excimer lamp 12 may be held with the vibration isolation member 18 as shown in FIG. 3 in order to suppress the creation of the gap between the external electrode and the discharge container by the vibration. In this way, holding the excimer lamp 12 with the vibration isolation member 18 leaves the excimer lamp 12 unaffected by the above-mentioned vibration, suppressing the creation of the above-mentioned gap. This configuration suppresses fluctuation in the illuminance of ultraviolet light emitted from the excimer lamp and enables stable ultraviolet light irradiation. The vibration isolation mechanism for suppressing the vibration of the excimer lamp is not limited to the above-mentioned vibration isolation member 18; however, it can apply to other configurations.

In addition, in the inactivation devices 100A to 100C described above, the excimer lamps, which are an ultraviolet light source, preferably use KrCl excimer lamps emitting ultraviolet light having a peak wavelength of 222 nm, or KrBr excimer lamps emitting ultraviolet light having a peak wavelength of 207 nm. The wavelength band of ultraviolet light used for decontamination (disinfection) applications is practically from 200 nm to 320 nm. In particular, ultraviolet light around 260 nm, which is highly absorbed by nucleic acids (DNA and RNA) possessed by microorganisms and viruses, is typically used. However, such ultraviolet light in the wavelength band around 260 nm has adverse effects on humans and animals, such as erythema, induction of cancer due to DNA damage in the skin, and eye damage (eye pain, redness, inflammation of cornea, etc.).

Hence, the ultraviolet light irradiation systems that use ultraviolet light around 260 nm for decontamination (disinfection) as described above are configured, with considering safety on humans and animals, to perform the ultraviolet light irradiation during the absence of humans and animals, and to stop the ultraviolet light irradiation during the presence of humans in the irradiation area. However, persons (infected persons) and animals with harmful microorganisms and/or viruses entering and leaving a space may often cause harmful microorganisms in the space to multiply, float, and adhere to the surfaces surrounding the space. Hence, an ultraviolet light irradiation system for decontamination (disinfection) is essentially effective in decontaminating not only the space and surfaces surrounding the space but also the surfaces of persons and animals present in the area.

The present inventors, after diligent research, have found that light in the wavelength range from 200 nm to 240 nm is safe for humans and animals and is capable of disinfecting microorganisms and inactivating viruses.

Figure 7:
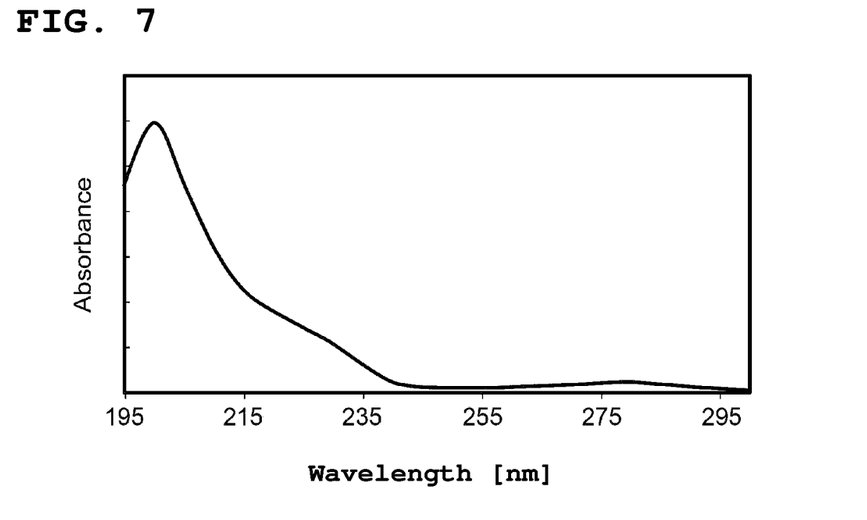
FIG. 7 is a graph illustrating the absorption spectrum of ultraviolet light on proteins.

FIG. 7 is a graph illustrating the absorption spectrum of ultraviolet light on proteins. As shown in FIG. 7, proteins exhibit an absorption peak at a wavelength of 200 nm and are less likely to absorb ultraviolet light having a wavelength of 240 nm or more. In other words, ultraviolet light having a wavelength of 240 nm or more easily transmits human skin and penetrates the skin. Hence, cells inside human skin are prone to damage. In contrast, ultraviolet light having a wavelength of around 200 nm is easily absorbed by the surface of human skin (e.g., stratum corneum) and is difficult to penetrate the skin. Hence, it is safe for the skin. On the other hand, ultraviolet light having a wavelength of less than 200 nm can generate ozone ($O_3$). This is because when ultraviolet light having a wavelength of less than 200 nm radiates in an atmosphere containing oxygen, oxygen molecules are photolysed to produce oxygen atoms, resulting in generating ozone through a bonding reaction between oxygen molecules and oxygen atoms.

Accordingly, the wavelength range from 200 nm to 240 nm is safe for humans and animals. The wavelength range that is safe for humans and animals is preferably from 200 nm to 237 nm, more preferably from 200 nm to 235 nm, and even more preferably from 200 nm to 230 nm. In other words, ultraviolet light with a wavelength of 222 nm emitted from KrCl excimer lamps and ultraviolet light with a wavelength of 207 nm emitted from KrBr excimer lamps are both safe for humans and animals and are capable of disinfecting microorganisms and inactivating viruses. Therefore, even if persons or animals are present in the disinfection and inactivation area in the space, the ultraviolet light irradiation can perform the disinfection and inactivation work.

ACGIH (American Conference of Governmental Industrial Hygienists) standard and JIS Z 8812 (Measuring Methods of Eye-hazardous Ultraviolet Radiation) set the threshold limit value (TLV) for the irradiation amount of ultraviolet light per day (8 hours) to human bodies in accordance with the wavelength band. Hence, in the above-mentioned inactivation devices 100A to 100C, it is recommended that the illuminance and irradiation time of ultraviolet light are determined such that the irradiation amount of ultraviolet (cumulative light intensity) per day is within the above threshold limit value.

As described above, the inactivation device in the present embodiment is provided with the ultraviolet light irradiation unit 10 supported by a supporter with vibration. Specifically, the inactivation device is provided with a mobile body (flying object 110, mobile body 120) that is movable in a space where a person is present, and a drive section that drives the mobile body. The ultraviolet light irradiation unit 10 is supported by the supporter provided in the above mobile body. The inactivation device in the present embodiment uses excimer lamps, which are less susceptible to vibration, as an ultraviolet light source emitting light containing ultraviolet light of wavelengths that inactivate microorganisms and/or viruses. Hence, even if the ultraviolet light source is subject to vibration during the flight of the flying object 110 or the movement of the mobile body 120, the ultraviolet light source can stably emit ultraviolet light. Therefore, the ultraviolet light irradiation unit 10 can suitably inactivate harmful microorganisms and/or viruses in a space or on surfaces surrounding the space while moving the ultraviolet light irradiation unit 10 in any three-dimensional or two-dimensional direction together with the flying object 110 or the moving object 120.

In addition, since the inactivation device of the present embodiment emits ultraviolet light having a wavelength range from 200 nm to 240 nm, which has less adverse effects on human and animal cells, irradiating even a person with the ultraviolet light enables disinfection and inactivation in a space where a person is present. Furthermore, the inactivation device of the present embodiment can be designed to set the wavelength of ultraviolet light emitted from the ultraviolet light source in a wavelength range from 200 nm to 237 nm and can be provided with an optical filter that blocks the transmission of UV-C waves with wavelengths longer than 237 nm. This can prevent damage to persons irradiated with the ultraviolet light even if they are irradiated with the ultraviolet light.

Since viruses attach to particles drifting in the air and diffuse, it is effective to irradiate particles that cause Mie scattering (Mie scattering) with ultraviolet light. Hence, in the inactivation device of the present embodiment, the controller 17 may control the ultraviolet light source section to irradiate particles that cause Mie scattering with ultraviolet light. This effectively suppresses viruses or other pathogens from attaching to particles drifting in the air and diffusing. In this case, the ultraviolet light may radiate after detecting the presence of particles with an optical sensor that detects Mie scattering.

(Variation Example)

In the excimer lamps 12 and 12A with the configurations shown in FIGS. 4A and 5A, respectively, the external electrode (external electrode 15 in FIG. 4A, outer electrode 15A in FIG. 5A) may be formed in the following manners such that a conductive paste containing glass powder and conductive metal powder, which is mainly composed of corrosion-resistant metallic materials such as gold, silver, copper, nickel, and chromium, is applied to the external surface of the discharge container by screen printing, for example, and then dried and fired. The external electrode may also be formed by the vacuum evaporation of the above metallic materials. Forming the external electrode in this way also prevents a gap from being created between the external electrode and the discharge container due to vibration.

Figure 8:
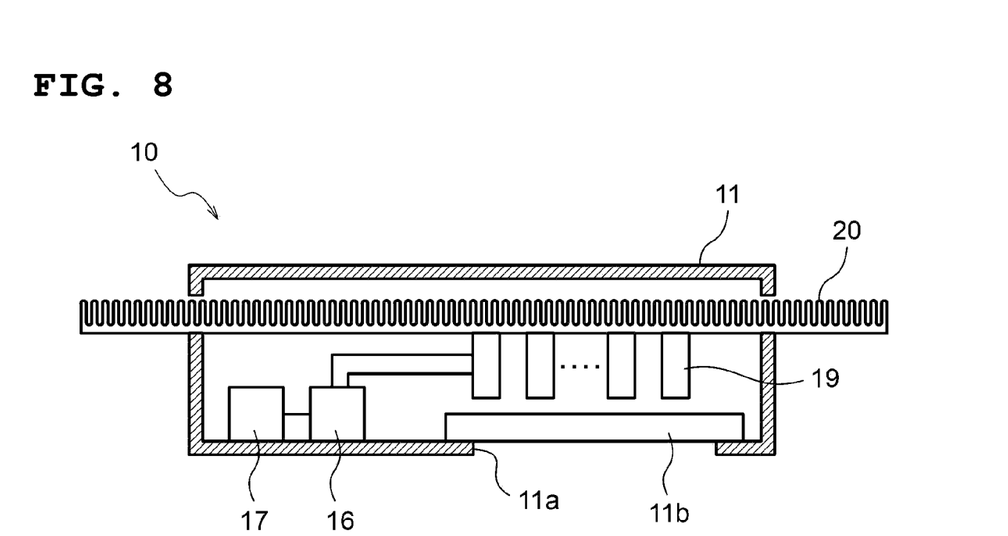
FIG. 8 is a schematic diagram illustrating another example of an ultraviolet light irradiation unit.

In the above embodiment, described is the case where an excimer lamp is used as an ultraviolet light source; however, an LED can also be used as an ultraviolet light source. An LED is also less susceptible to vibration similar to an excimer lamp. FIG. 8 shows an example of the ultraviolet light irradiation unit 10 using an LED 19 as an ultraviolet light source. In FIG. 8, the ultraviolet light irradiation unit 10 is provided with the plurality of LEDs 19.

As mentioned above, the wavelength band of ultraviolet light used for decontamination (disinfection) applications is from 200 nm to 320 nm, and a particularly effective wavelength is around 260 nm, which is highly absorbed by nucleic acids (DNA, RNA). Hence, the LED 19, which is an ultraviolet light source mounted in the ultraviolet light irradiation unit 10, is also selected such that the LED 19 emits ultraviolet light having a wavelength of 200 nm to 320 nm. Specifically, examples of the LED 19 include aluminum-gallium-nitride (AlGaN)-based LEDs and aluminum-nitride (AlN)-based LEDs. AlGaN-based LEDs can emit light in the deep-ultraviolet (deep UV: DUV) band in a wavelength range from 200 nm to 350 nm by changing the composition of aluminum (Al). In addition, AlN-based LEDs emit ultraviolet light having a peak wavelength of 210 nm.

Here, in AlGaN-based LEDs, the composition of Al is preferably adjusted such that the center wavelength is in a range from 200 nm to 237 nm. As described above, ultraviolet light in this wavelength range is safe for humans and animals, and can suitably disinfect microorganisms and inactivate viruses. For example, adjusting the composition of Al enables AlGaN-based LEDs to emit ultraviolet light having a center wavelength of 222 nm.

In addition, magnesium-zinc-oxide (MgZnO)-based can also be used as the LED 19. The MgZnO-based LEDs emit light in the deep-ultraviolet band (deep UV: DUV) in a wavelength range from 190 nm to 380 nm by changing the composition of magnesium (Mg).

Here, in MgZnO-based LEDs, the composition of Mg is preferably adjusted such that the center wavelength is in a range from 200 nm to 237 nm. As described above, ultraviolet light in this wavelength range is safe for humans and animals and can suitably disinfect microorganisms and inactivate viruses. For example, adjusting the composition of Mg enables MgZnO-based LEDs to emit ultraviolet light having a center wavelength of 222 nm.

Here, LEDs emitting the above-mentioned ultraviolet light (particularly ultraviolet light in the deep-ultraviolet band) have a low luminous efficiency of several percent or less, generating a large amount of heat. When the heat generation of the LEDs increases, the intensity of the light emitted from the LEDs decreases, and the wavelength of the emitted light also shifts. Hence, as shown in FIG. 8, the LEDs 19 are preferably mounted in a cooling member 20 (e.g., heat sink with fins to dissipate heat) to suppress the increase in the temperature of the LEDs 19. At this time, as shown in FIG. 8, a part of the cooling member 20 may be protruded from the enclosure 11 of the ultraviolet light irradiation unit 10.

Figure 9:
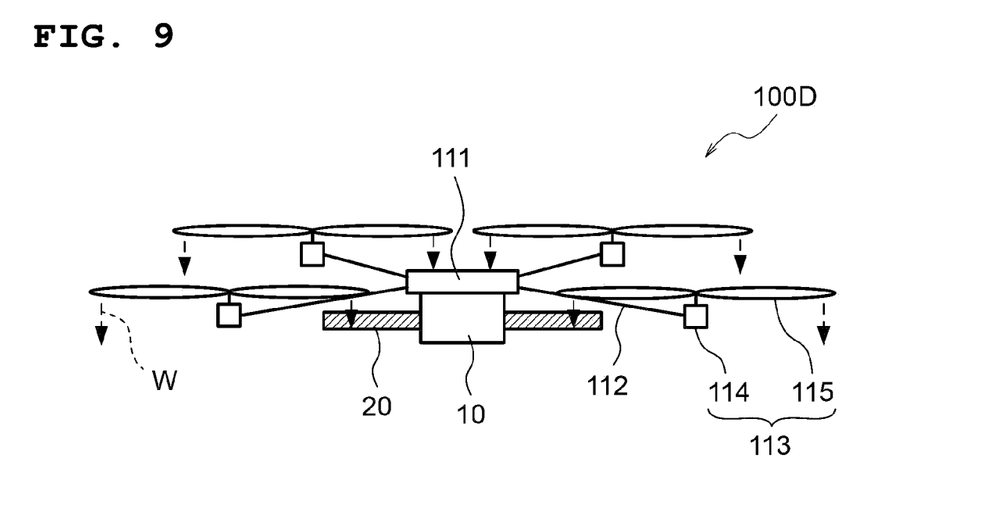
FIG. 9 is a schematic diagram illustrating another example of an inactivation device in which an ultraviolet light irradiation unit is mounted on a flying object.

When the ultraviolet light irradiation unit 10 shown in FIG. 8 is mounted on a flying object (e.g., a drone) like an inactivation device 100D as shown in FIG. 9, part of the cooling member 20 can be exposed to the exhaust flow from the rotor blades 115. In this way, the exhaust flow hitting part of the cooling member 20 allows the cooling member 20 to dissipate heat more efficiently, suitably suppressing the increase in the temperature of the LEDs 19.

Note that the above-mentioned AlGaN-based LEDs and MgZnO-based LEDs emitting ultraviolet light having a center wavelength of 222 nm emit ultraviolet light having a broad wavelength range from the center wavelength of 222 nm to a certain extent. The light emitted from these LEDs contains a small amount of ultraviolet light having wavelengths that are unsafe for humans and animals. Hence, it is preferable to use a dielectric multilayer filter (optical filter) that blocks light in the UV-C wavelength band having wavelengths other than 200 nm to 237 nm, as is the case when the ultraviolet light source is an excimer lamp. The above optical filter may be more preferably a filter that blocks light with the UV-C wavelength band having wavelengths other than 200 nm to 235 nm, and may be further preferably a filter that blocks light with the UV-C wavelength band having wavelengths other than 200 nm to 230 nm. This holds true even when the light source is an excimer lamp.

However, the above optical filter is unnecessary for the above AlN-LEDs emitting ultraviolet light having a center wavelength of 210 nm. In addition, there may be a case in which the illuminance at the irradiated surface of the ultraviolet light having wavelengths unsafe for humans and animals is less than the allowable value when the ultraviolet light source is an excimer lamp or an LED. This depends on, for example, the illuminance on the light-emitting surface of the ultraviolet light source or the distance from the ultraviolet light source to the surface illuminated with ultraviolet light. Hence, the above optical filter is unnecessary for this case.

In the above embodiments, described are the cases in which the ultraviolet light irradiation unit 10 is mounted on a mobile body that is movable in a space where a person is present, and is made to move together with the mobile body in the space to irradiate the space with ultraviolet light, such as the flying object 110 in FIG. 1 and the moving object 120 in FIGS. 2A and 2B. However, the configuration of the inactivation device is not limited to the above embodiment. The ultraviolet light irradiation unit 10 can be mounted, for example, in a mobility means for transporting persons or objects in a space where a person is present.

Here, the above mobility means can be, for example, aircraft, bullet trains or other trains, buses, cabs, or other transportation means. The space where a person is present in the above mobility means can be cabins or restrooms in aircraft or trains, or spaces in buses or cabs. In this case, too, the ultraviolet light irradiation unit 10 is subject to vibration during the movement of the mobility means, but the ultraviolet light source can stably emit ultraviolet light. Setting the ultraviolet light irradiation unit 10 in a space where persons enter and leave, such as cabins or restrooms makes it possible to effectively suppress the infection of viruses to other persons who enter the space.

Furthermore, excimer lamps and LEDs have features that are less affected by changes in pressure or temperature in addition to the above-described vibration. Sudden changes in pressure or temperature are transmitted to the lamps and other devices in the form of physical shocks due to air pressure and thermal expansion of materials, causing the same phenomenon as the vibration described above. Hence, using excimer lamps or LEDs as the ultraviolet light source enables ultraviolet light to be stably emitted even when the inactivation device is used in an environment subject to vibration, changes in air pressure, and changes in temperature. In other words, it is possible to suppress fluctuation in the illuminance of the ultraviolet light emitted from the ultraviolet light source even when the inactivation device is subjected to changes in air pressure in cabins during aircraft flights, changes in air pressure caused by changes in the altitude of flying objects, or changes in air pressure occurred in high-speed trains, such as bullet trains, passing through tunnels.

The specific embodiments have been described above; however, the present embodiments are merely examples and are not intended to limit the scope of the present invention. The devices and methods described herein can be embodied in forms other than those described above. Also, without departing from the scope of the present invention, omissions, substitutions, and modifications may be made to the above embodiments as appropriate. Such embodiments with omissions, substitutions, and modifications are included in the scope of the claims and their equivalents, and belong to the technical scope of the present invention.

10 Ultraviolet light irradiation unit
11 Enclosure
12 Excimer lamp
13 Discharge container
14 First electrode
15 Second electrode
16 Power supply
17 Controller
18 Vibration isolation member
19 LED
20 Cooling member
100A to 100C Inactivation device
110 Flying object
111 Body section
112 Frame section
113 Drive section
114 Motor
115 Rotor blade
120 Mobile body
121 Body section
122 Wheel
123 Supporter
124 Irradiation direction adjustment mechanism

The invention claimed is:

1. An inactivation device that inactivates microorganisms and/or viruses present in a space where a person is present by irradiating the space with ultraviolet light, the inactivation device comprising:
a mobile body movable in the space;
a drive section that drives the mobile body;
an ultraviolet light irradiation unit provided with an ultraviolet light source emitting light including ultraviolet light having a wavelength that inactivates the microorganisms and/or viruses; and
a controller that controls irradiation of the light from the ultraviolet light source,
the ultraviolet light included in the light emitted from the ultraviolet light source includes ultraviolet light having a wavelength range from 200 nm to 240 nm, and
the ultraviolet light irradiation unit is fixed to the mobile body, wherein the ultraviolet light source is an excimer lamp including a discharge container filled with gas for excimer luminescence and a pair of electrodes that make a dielectric barrier discharge generated inside the discharge container, and
at least one of the electrodes is printed or deposited on an outer surface of the discharge container.

2. The inactivation device according to claim 1, wherein the ultraviolet light irradiation unit includes an enclosure that houses the ultraviolet light source thereinside and that includes a light emission window through which at least a part of the light emitted from the ultraviolet light source is emitted, and the light emission window is provided with an optical filter that blocks transmission of UV-C waves having longer wavelengths than 237 nm.

3. The inactivation device according to claim 1, wherein the ultraviolet light source emits ultraviolet light having a center wavelength of 222 nm.

4. The inactivation device according to claim 1, wherein the ultraviolet light source is an excimer lamp, and the ultraviolet light irradiation unit includes an enclosure that houses the excimer lamp and is made of a conductive metal.

5. An inactivation device that inactivates microorganisms and/or viruses present in a space where a person is present by irradiating the space with ultraviolet light, the inactivation device comprising:
   a mobile body movable in the space;
   a drive section that drives the mobile body;
   an ultraviolet light irradiation unit provided with an ultraviolet light source emitting light including ultraviolet light having a wavelength that inactivates the microorganisms and/or viruses; and
   a controller that controls irradiation of the light from the ultraviolet light source,
   the ultraviolet light included in the light emitted from the ultraviolet light source includes ultraviolet light having a wavelength range from 200 nm to 240 nm, and
the ultraviolet light irradiation unit is fixed to the mobile body, wherein the ultraviolet light source is an excimer lamp including a discharge container filled with gas for excimer luminescence and a pair of electrodes that make a dielectric barrier discharge generated inside the discharge container,
   at least one of the electrodes is disposed to be in contact with the discharge container, and
   the ultraviolet light irradiation unit is provided with a vibration isolation mechanism that suppresses vibration of the excimer lamp.

6. The inactivation device according to claim 5, wherein the ultraviolet light irradiation unit includes an enclosure that houses the ultraviolet light source thereinside and that includes a light emission window through which at least a part of the light emitted from the ultraviolet light source is emitted, and the light emission window is provided with an optical filter that blocks transmission of UV-C waves having longer wavelengths than 237 nm.

7. The inactivation device according to claim 5, wherein the ultraviolet light source emits ultraviolet light having a center wavelength of 222 nm.

8. The inactivation device according to claim 5, wherein the ultraviolet light source is an excimer lamp, and the ultraviolet light irradiation unit includes an enclosure that houses the excimer lamp and is made of a conductive metal.

9. An inactivation device that inactivates microorganisms and/or viruses present in a space where a person is present by irradiating the space with ultraviolet light, the inactivation device comprising:
   a mobile body movable in the space;
   a drive section that drives the mobile body;
   an ultraviolet light irradiation unit provided with an ultraviolet light source emitting light including ultraviolet light having a wavelength that inactivates the microorganisms and/or viruses; and
   a controller that controls irradiation of the light from the ultraviolet light source,
   the ultraviolet light included in the light emitted from the ultraviolet light source includes ultraviolet light having a wavelength range from 200 nm to 240 nm, and
   the ultraviolet light irradiation unit is fixed to the mobile body, wherein the ultraviolet light source is at least an LED, and the ultraviolet light irradiation unit includes a cooling member having heat-dissipating fins and located above the LED for cooling the LED by being exposed the heat-dissipating fins to exhaust flow from the drive section.

10. The inactivation device according to claim 9, wherein the ultraviolet light irradiation unit includes an enclosure that houses the ultraviolet light source thereinside and that includes a light emission window through which at least a part of the light emitted from the ultraviolet light source is emitted, and the light emission window is provided with an optical filter that blocks transmission of UV-C waves having longer wavelengths than 237 nm.

11. The inactivation device according to claim 9, wherein the ultraviolet light source emits ultraviolet light having a center wavelength of 222 nm.

* * * * *